(12) United States Patent
Azuma

(10) Patent No.: US 7,655,466 B2
(45) Date of Patent: Feb. 2, 2010

(54) PRODUCTION PROCESS FOR MUNANT

(75) Inventor: Takachika Azuma, Lions Garden S401, 2361-1 Yamazaki, Noda-shi, Chiba (JP) 278-0022

(73) Assignees: Takachika Azuma, Chiba (JP); Otsuka Pharmaceutical Co., Ltd., Tokyo (JP)

( * ) Notice: Subject to any disclaimer, the term of this patent is extended or adjusted under 35 U.S.C. 154(b) by 1131 days.

(21) Appl. No.: 10/481,742

(22) PCT Filed: Jun. 25, 2002

(86) PCT No.: PCT/JP02/06341

§ 371 (c)(1),
(2), (4) Date: Dec. 23, 2003

(87) PCT Pub. No.: WO03/000885

PCT Pub. Date: Jan. 3, 2003

(65) Prior Publication Data

US 2004/0209268 A1    Oct. 21, 2004

(30) Foreign Application Priority Data

Jun. 25, 2001    (JP) .............................. 2001-191884

(51) Int. Cl.
*C12N 15/00*    (2006.01)
(52) U.S. Cl. .................... 435/440; 435/320.1
(58) Field of Classification Search ................ None
See application file for complete search history.

(56) References Cited

U.S. PATENT DOCUMENTS 5,885,827 A    3/1999    Wabl et al.

FOREIGN PATENT DOCUMENTS

WO    9010077 A1    9/1990

OTHER PUBLICATIONS

Azuma et al, *International Immunology*, 5(2):121-130 (1993).
Database EMBL XP002312949, Accession No. AC073563.3, Abstract (Jul. 3, 2000).
Database EMBL XP002313006, Accession No. X03571, Abstract (Nov. 18, 1986).
Database EMBL XP002312950, Accession No. S74164.1, Abstract (Mar. 4, 2000).
Database EMBL XP002312951, Accession No. S74166.1. Abstract (Mar. 4, 2000).
Azuma et al, *Immunological Reviews*, 162:97-105 (1998).
Tumas-Brumdage et al, *Molecular Immunology*, 34(5):367-378 (1997).
Madisen et al, *Genes Dev.*, 8(18):2212-2226 (1994).
Kanda et al, *J. Biol. Chem.*, 275(14):32338-32346 (2000).
Loh et al, *Cell.*, 33(1):85-93 (1983).
Terauchi et al, *J. of Immunology*, 167:811-820 (2001).
Azuma et al, *International Immunology*, 5(2):121-130 (1992).
Lieberson et al, *The EMBO Journal*, 14(24):6229-6238 (1995).
Arulampalam et al, *Review: Immunology Today*, 18(11):549-554 (1997).

*Primary Examiner*—James S Ketter
(74) *Attorney, Agent, or Firm*—Sughrue Mion, PLLC

(57) ABSTRACT

The invention provides a production process for a high-frequent random mutant of an object exogenous gene, wherein a recombinant expression vector in which a eukaryote promoter, an exogenous DNA sequence, an intron enhancer and 3'HS3/4 enhancer are linked is introduced and expressed in an animal cell.

16 Claims, 5 Drawing Sheets

PRODUCTION PROCESS FOR MUNANT

TECHNICAL FIELD

The present invention relates to a novel production process for a mutant comprising introducing a improved DNA construct into animal cells, the DNA construct, and a kit for producing a gene mutant or expressing a mutant gene.

BACKGROUND ART

Living things now in existence have evolved over a long period of time through the mutatagenesis and the selection of mutants by the environment. The general evolution has very slow speed and passes through many generations to advance. On the other hand, in the case of antibody-producing cells of the immune system, the mutatagenesis and the selection by antigens are completed in one generation, and the next generation will not inherit the acquired function. Such a quick rate of evolution in the immune system is interpreted as being set against the mutation of an environment-dependent pathogenic microorganism.

The present inventor previously produced transgenic mice to which genes of bacteria-derived enzyme chloramphenicol acetyltransferase are introduced, and demonstrated that the mutation of an antibody gene is controlled by its promoter and enhancer and the mutation of any genes can be induced by controlling with a promoter and enhancer of an antibody gene (Azuma, T., et al., Int. Immunology, 5(2) 121-130 (1992)).

The currently used production process for a mutant is one of the mutant-producing methods in which deletion, insertion and/or addition mutation is suitably introduced into a desired DNA sequence, that is, site-specific mutagenesis to site-specifically replace a certain length of DNA sequences (Site-specific mutagenesis, Zoller, et al., Nucleic Acid Res., 10, 6487-6500 (1982); Zoller, et al., Methods in Enzymol., 100, 468-500 (1983))). In the general mismatch mutation using an artificially synthesized oligonucleotide as a primer, a complementary oligonucleotide consisting of around 20 bases is synthesized with an optional mutation in a base sequence nearby a site where mutation is to be induced, the oligonucleotide is hybridized to a target DNA, and then a DNA complementary to the remaining of target DNA can be produced using DNA polymerase. Thus it is possible to introduce a desired mutation into a desired site. However, this method cannot induce many mutants at once.

In the other mutagenesis systems, some examines the disappearance or the manifestation of a specific function in the presence of a compound that damages a gene (Myers, et al., Science, 232, 613-618 (1986)), and other uses bacteria etc. However, these methods are fundamentally different from the above one to induce mutation by the present inventor.

Variation (diversity) in the Ig V region of mice and humans is generated by the combinatorial joining of V, D, and J gene segments existing separately in germline, the deletion and addition of nucleotides at the junction of these segments during joining, and somatic hypermutation of joined V-(D)-J genes. The somatic hypermutation is related to the affinity maturation of antibody and has been frequently observed after stimulation of T cell-dependent antigen (TD) (Bothwell, A. L. M., et al., Cell, 24, 625 (1981): Gearhart, P. J., et al., Nature, 291, 29 (1981): Griffiths, G. M., et al., Nature, 312, 271 (1984): Maizels, N., et al., Cell, 43, 715 (1985): Wysocki, L. T., et al., Proc. Natl. Acad. Sci. USA, 83, 1847 (1986): Cumano, A., et al., EMBO. J., 5, 2459 (1986): Berek, C., et al., Cell, 67, 1121 (1991): Taketani, M., et al., Mol. Immunol., 32, 983 (1995): Furukawa, k., et al., Immunity, 11, 329 (1999): 2-10). The cis-acting elements responsible for the induction of somatic hypermutation have been identified using κ-chain (O'Brien, R. L. et al., Nature, 326, 405 (1987): Sharpe, M. J., et al., Eur. J. Immunol., 20, 1379 (1990): Sharpe, M. J., et al., EMBO J., 10, 2139 (1991): Betz, A. G., et al., Cell, 77, 239 (1994): Yelamos, J., et al., Nature, 376, 225 (1995): Peters, A., et al., Immunity, 4, 57 (1996): 11-16), λ-chain (Klotz, E., et al., J. Immunol., 157, 4458 (1996):17) and H-chain transgenic mice (Durdik, J., et al., Proc. Natl. Acad. Sci. USA, 86, 2346 (1989): Sohn, J., et al., J. Exp. Med., 177, 493 (1993): Tumas-Brundage, K. M. and Manser, T., J. Exp. Med., 185, 239 (1997):18-20).

As stated above, the present inventor prepared transgenic mice carrying chloramphenicol acetyltransferase (CAT) gene that is driven by $V_H1$7.2.25 (Loh, D. Y., et al., Cell, 33, 85 (1983): Grosschedl, R. and Baltimore, D., Cell, 41, 885 (1985): 22, 23) and J-C intron enhancer (hereafter abbreviated to Eμ) (Gillies, S. D., et al., Cell, 33, 715 (1983): Banerji, J., et al., Cell, 33, 729 (1983):24, 25)/matrix attachment region (hereafter abbreviated to MAR) (Forrester, W. C., et al., Science, 265, 1221 (1994):26). As a result, somatic hypermutation was detected in CAT but not in $V_H$ promoter or Eμ/MAR flanking. However, the frequency of mutation was approximately 1/10 that observed in endogenous $V_H$-D-$J_H$, suggesting that these cis-acting elements are critical or important for the induction of hypermutation and that other components such as Cγ, Cα of 3' or the enhancer flanking of Cα (3' enhancer) (Pettersson, S., et al., Nature, 344, 165 (1990): Dariavach, P., et al., Eur. J. Immunnol., 21, 1499 (1991): Lieberson, R., et al., EMBO. J., 14, 6229 (1995):27-29) might be responsible for high frequent somatic hypermutation (Sohn, J., et al., J. Exp. Med., 177, 493 (1993): Tumas-Brundage, K. M. and Manser, T., J. Exp. Med., 185, 239 (1997): Giusti, A. M. and Manser, T., J. Exp. Med., 177, 793 (1997): 19, 20, 30).

DISCLOSURE OF THE INVENTION

In order to identify the component(s) important in raising the frequency of hypermutation in IgH gene, the present inventor employed a RAG-2-deficient (Recombination Activating Gene: gene rearrangement protein-2 blastocyst complementation system developed by Chen et al. (Chen, J., et al., Proc. Natl. Acad. Sci. USA, 90, 4528 (1993):31). A series of transgene constructs differed only in the 3'-flanking region were microinjected into RAG-2-deficient blastocysts to transfect embryonic stem cells (hereafter abbreviated to ES cells). The chimeric mice obtained in this system were immunized with a T cell-dependent antigen.

As a result, the frequency of somatic hypermutation in $V_H$-D-$J_H$ of the transgene revealed that the insertion of DNaseI sensitive region 3b (hereafter HS3b) and/or HS4 (Madisen, L. and Groudine, M., Genes Dev. 8, 2212 (1994): Michaelson, J. S. et al., Nucleic Acids Res., 23, 975 (1995): Arulampalam, V. et al., Immunol. Today, 18, 549 (1997):32-34) induces random somatic hypermutation.

An object of the present invention is to provide a production process for a random mutant, where a DNA construct in which a modified eukaryotic promoter, an external DNA sequence, an intron enhancer and a 3' HS3/4 enhancer are linked is introduced into an animal cell. Another object of the present invention is to provide a method for obtaining a mutant gene by expressing the DNA construct in an animal cell. The inventor found a DNA construct for producing such mutant and a kit for producing a gene mutant or expressing the mutant, thus to accomplish the present invention. Further, a mutant expression product obtained from the expression system using animal cells is to mean that it has subjected to the screening for toxicity against animal cells.

The present invention provides the following Items 1 to 20.

Item 1. A production process for an exogenous gene random mutants, wherein a DNA construct comprising at least the following (a)-(d) is introduced into an animal cell and the exogenous gene mutant is produced in the animal cell:

(a) a promoter;
(b) an exogenous gene;
(c) an intron enhancer; and
(d) an enhancer comprising HS3b and/or HS4 in a DNaseI sensitive region.

Item 2. The production process according to Item 1, wherein the (d) enhancer further comprises HS1 and HS2.

Item 3. The production process according to Item 1 or 2, wherein the (d) enhancer has a DNA sequence comprising at least a DNA sequence of SEQ ID NO: 1 or 2.

Item 4. The production process according to any one of Items 1 to 3, wherein DNA sequences of (a), (c) and (d) are derived from a DNA sequence of an immunoglobulin Item 5. The production process according to Item 2, wherein the (d) enhancer comprises HS1, HS2, HS3b and HS4.

Item 6. The production process according to any one of Items 1 to 5, wherein the (a) promoter is a $V_H$ promoter; and the (d) enhancer has a DNA sequence comprising DNA sequences of SEQ ID NOs: 1 and 2.

Item 7. The production process according to Item 5 or 6, wherein the DNA construct is pvehc3'EHS3b/4.

Item 8. The production process according to any one of Items 1 to 7, wherein the animal cell is a B cell line animal cell.

Item 9. The production process according to Item 8, wherein the B cell line animal cell is derived from a pre-B lymphocyte line cell.

Item 10. A method for obtaining an expression product of a mutant gene by expressing the exogenous gene mutant obtained by the method according to any one of Items 1 to 9 in the animal cell.

Item 11. A DNA construct for producing an exogenous gene mutant, comprising at least:

(a) a promoter;
(b) an exogenous gene;
(c) an intron enhancer; and
(d) an enhancer comprising HS3b and/or HS4 in a DNaseI sensitive region.

Item 12. The DNA construct according to Item 11, wherein the (d) enhancer further comprises HS1 and HS2.

Item 13. The DNA construct according to Item 11 or 12, wherein the (d) enhancer has a DNA sequence comprising at least a DNA sequence of SEQ ID NO: 1 or 2.

Item 14. The DNA construct according to any one of Items 11 to 13, wherein DNA sequences of (a), (c) and (d) are derived from a DNA sequence of immunoglobulin.

Item 15. The DNA construct according to any one of Items 11 to 14, wherein the (d) enhancer comprises HS1, HS2, HS3b and HS4.

Item 16. The DNA construct according to any one of Items 11 to 15, wherein the (a) promoter is a $V_H$ promoter; and the (d) enhancer has a DNA sequence comprising DNA sequences of SEQ ID NOs: 1 and 2.

Item 17. The DNA construct according to Item 11 or 12, wherein the DNA construct is pvehc3'EHS3b/4.

Item 18. A kit for production process of an exogenous gene mutant or producing an expression product of a mutant gene, comprising a vector having:

(a) a promoter;
(b) an exogenous gene-insertion site;
(c) an intron enhancer; and
(d) an enhancer comprising HS3b and/or HS4 in a DNaseI sensitive region;

for achieving an expression of a mutated DNA sequence which produces an exogenous gene mutant.

Item 19. The kit according to Item 18, wherein the (d) enhancer further comprises HS1 and HS2.

Item 20. $V_H$17.2.25 promoter having a sequence of SEQ ID NO: 14.

According to the present invention, an exogenous gene is introduced into the system controlled by the promoter and enhancer of an antibody gene, and therefore a gene cluster having frequent and random mutations can be obtained and a production process for an animal cell line mutant in which a mutation is widely introduced into a peptide or protein is provided, thus it is possible to try to improve and change a function of naturally occurring protein. For example, it becomes possible to develop new type of antibiotics having an improved function against antibiotic resistant bacteria, agricultural chemicals, or improved peptide pharmaceuticals having a better function such as interferon and growth hormone. Moreover, by using animal cells, it is possible to carry out a toxicity screening on animal cells simultaneously, and therefore the primary toxicity can be examined and the quick creation of various peptide products having a functionally improved action is attained.

Hereafter in this specification, the representation of amino acids, peptides, base sequences, nucleic acids and the like by abbreviation shall follow the provision of IUPAC-IUB (IUPAC-IUB Communication on Biological Nomenclature, Eur. J. Biochem., 138: 9 (1984)), "Guideline for the preparation of specification and others containing a base sequence or an amino acid sequence" (edited by the Japanese Patent Office) and the conventional symbols in the art.

The synthesis of DNA, the construction of DNA construct containing an exogenous gene (e.g., an expression vector), the preparation method of a host cell transformed by the DNA construct and an expressed protein secreted by a host cell, etc. can be easily prepared or obtained in accordance with general genetic engineering techniques (Molecular Cloning 2d Ed, Cold Spring Harbor Lab. Press (1989); Continuation of Biochemical Experiment Course, Genetic Research Method I, II and III, Japanese Biochemical Society (1986)) or gene recombination techniques (refer to e.g., Science, 224, 1431 (1984); Biochem. Biophys. Res. Comm., 130, 692 (1985); Proc. Natl. Acad. Sci. USA., 80, 5990 (1983)).

In the present invention, a mutant refers to a gene comprising a random mutated DNA sequence of an exogenous gene or an expression product having a mutated amino acid sequence encoded by a random mutated gene.

The mutant production in an animal cell according to the invention can be achieved by preparing a DNA construct provided by the invention for inducing mutant (recombinant DNA) that can be expressed in a host cell containing a gene encoding a desired protein, and introducing the construct into the cell.

In the specification "introduce a DNA construct into an animal cell" means to incorporate an exogenous gene into a genome of animal cell.

The expression product of mutant is obtained by cultivating a transformant containing the above mutant of exogenous gene and then collecting the product from the resulting culture.

The DNA construct for inducing mutant provided by the present invention has a structure comprising at least (a) a promoter, (b) an exogenous gene, (c) an intron enhancer, and (d) an enhancer containing HS1, HS2 and HS3b and/or HS4 in a DNaseI sensitive region and can be easily produced or obtained by general gene engineering technique.

For the preparation of each gene (DNA) in the invention, the gene may be derived from a suitable origin or chemically synthesized.

Specifically, the DNA synthesis may be chemical synthesis based on the phosphoramidite method or the triester method, or may be carried out on the commercially available automatic oligonucleotide synthesizer. A double strand fragment can also be prepared from a chemically synthesized single strand product by: synthesizing complementary strands and annealing these strands together under suitable conditions; or using a DNA polymerase together with a suitable primer sequence to add a complementary strand.

In addition, each gene can be obtained by: either DNA synthesis as described above; or preparing a cDNA library in accordance with an ordinary method from a vector containing the gene or from a suitable origin in which the gene is expressed, and selecting a desired clone using suitable probe or antibody specific to the gene (Proc. Natl. Acad. Sci. USA, 78, 6613 (1981); Science, 222, 778 (1983) etc).

Illustrated as the origin of cDNA in the above are various kinds of cells and tissues where each gene is expressed, cultured cells derived therefrom and the like. In addition, separation of total RNA from these origins, separation and purification of mRNA, preparation and cloning of cDNA, etc. can be all performed in accordance with an ordinary method. Commercially available cDNA libraries such as cDNA library from Clontech Lab. Inc. can be used in this invention. A method of screening the gene from cDNA library is not limited and can be performed in accordance with an ordinary method.

Specifically, a method of immunoscreening the proteins produced by cDNA using specific antibodies against the proteins and selecting the corresponding cDNA clone, plaque hybridization and colony hybridization with the use of a probe selectively combined with a target DNA sequence, a combination of these methods, etc. can be used.

As the probe used herein, a DNA chemically synthesized based on the information of the base sequence of each gene can be generally used, but a gene already obtained according to the invention or a fragment thereof can also be used satisfactorily. Sense primer or antisense primer designed based on the base sequence information of exogenous gene can be used as a probe for screening.

A partial nucleotide sequence corresponding to the DNA sequence of each gene is used as the above-mentioned probe. The nucleotide sequence may contain at least 15 serial bases, preferably 20 serial bases, more preferably 30 serial bases, and most preferably 50 serial bases. Alternatively, a positive clone containing said sequence itself may be used as a probe.

The DNA/RNA amplification by the PCR method (Science, 230, 1350 (1985)) can be preferably employed for obtaining a gene. Especially, when it is difficult to obtain full length of cDNA from the library, RACE method (Rapid amplification of cDNA ends; Journal of Experimental Medicine, 12(6), 35 (1994)), especially 5'-RACE method (M. A. Frohman et al., Proc. Natl. Acad. Sci. USA., 8, 8998 (1988)), etc. can be preferably adopted.

When the PCR method is adopted, the primer used may be designed based on the gene sequence information and synthesized in accordance with an ordinary method. The amplified DNA/RNA fragment may be separated and purified in accordance with an ordinary method as described above, for example gel electrophoresis.

The sequences of the genes or various kinds of DNA fragments obtained above may be determined in accordance with an ordinary method, for example the dideoxy procedure (Proc. Natl. Acad. Sci. USA., 74, 5463 (1977)) and the Maxam-Gilbert Method (Methods in Enzymology, 65, 499 (1980)), or more easily using a commercial sequencing kit and the like.

(b) Desired Exogenous Gene

In the constituents of the above-described DNA construct, the DNA used as (b) exogenous gene may be either an exogenous DNA sequence derived from a desired gene or an expressed protein which is a basis for inducing a mutant. Or the DNA used as exogenous gene may be synthesized. The length of the exogenous gene used for the present production process for a mutant may be generally 4 Kb or less, preferably 3 Kb or less, more preferably around 2 Kb, but an exogenous DNA sequence having the length more than 4 Kb can be also used.

The exogenous gene is not especially limited insofar as it exhibits a biological activity when expressed. For example, growth hormone (GH), insulin, interferon, erythropoietin, etc. can be illustrated.

For the easier checking of the insertion of exogenous gene into a genome of host cell, the DNA sequence of a gene to be used as a so-called marker may be linked to the DNA sequence of the above (b) exogenous gene.

By using a part or the entire base sequences of thus obtained exogenous gene, the expression of exogenous gene and its mutant in an individual or various tissues can be detected with specificity.

Such detection can be carried out in accordance with an ordinary method, for example, RNA amplification by RT-PCR (Reverse transcribed-Polymerase chain reaction; E. S. Kawasaki, et al., Amplification of RNA. In PCR Protocol, A Guide to methods and applications, Academic Press, Inc., San Diego, 21-27 (1991)), Northern Blotting analysis (Molecular Cloning, Cold Spring Harbor Lab. (1989)), detection at cell-level using in situ RT-PCR (Nucl. Acids Res., 21, 3159-3166 (1993)) and in situ hybridization, NASBA method (Nucleic acid sequence-based amplification, Nature, 350, 91-92 (1991)) and the other various method. The detection by RT-PCR is preferably illustrated.

The DNA fragment of the exogenous gene is provided in the form of a restriction fragment cleaved with a suitable restriction enzyme, that is (b) exogenous gene of the DNA construct.

(a) Promoter

Examples of (a) promoter used as a constituent of the above-mentioned DNA construct include an immunoglobulin heavy chain variable region promoter ($V_H$ promoter), a promoter derived from SV 40, a retrovirus promoter, an adenovirus promoter, a cytomegalovirus promoter, a promoter derived from viruses such as polyoma virus or hepatitis B virus, a metallothionein promoter, a heat shock promoter, a SRα promoter, other promoters effective for the mammalian cell, etc. $V_H$ promoter, specifically $V_H$17.2.25 promoter (Gillies, S. D., et al., Cell, 33, 715 (1983): Banerji, J., et al., Cell, 33, 729 (1983)) are preferably used in this invention.

The above promoters may include, for example, a promoter that can induce a neomycin resistance gene or a tetramycin resistance gene.

The above promoters may be in the linked form of two or more.

These various DNA sequences of the above promotera are known and the information thereof is available.

(c) Intron Enhancer

An intron enhancer is a DNA sequence that can adjust the transcription and contains the sequence of unexpressed region intervening between the exons of heavy chain JH gene and Cμ gene. Heavy chain enhancer (Cμ enhancer) and kappa chain enhancer (κ enhancer) of immunoglobulin can be illustrated as (c) intron enhancer.

(d) Deoxyribonuclease I (DNaseI) Sensitive Region

A DNaseI sensitive region is a region that undergoes fragmentation when the nucleus of an isolated cell is treated with a low concentration of DNaseI. In the case of immunoglobulin heavy chain gene, HS1, HS2, HS3b and HS4 are known. HS3b/4 is both or either of HS3b and HS4. This invention is characterized in that HS3b region and/or HS4 region are/is contained. In a preferable embodiment, HS1 and HS2 (these are referred to as 3'E) in addition to HS3b and/or HS4 are included. Illustrated as a 3'EHS3b/4 is a sequence without intron sequences, comprising XbaI fragment (4.0 kb) from 3' enhancer disclosed by Lieberson, R. et al. (EMBO. J., 14, 6229 (1995)) and HS3 (1182 bp) and HS4 (1381 bp) from MP11 disclosed by Madisen, L. et al. (Genes Dev., 8, 2212 (1994)).

Connection of Each Gene (Preparation of DNA Construct)

The DNA construct of the invention can be prepared for example by inserting each of the above-described genes into a suitable expression vector in accordance with an ordinary method, for example by inserting each element into a vector having suitable antibiotic resistance gene. Specifically, the DNA construct can be constructed by inserting the promoter, the exogenous gene, the intron enhancer, the DNaseI sensitive region (including DNA sequences of HS3b and/or HS4 and if necessary further including an enhancer comprising 3'E), which are cut out from a vector clone, a genomic DNA or a plasmid by an optional restriction enzyme or synthesized, into a vector used for animal cell line having an optional antibiotic resistance gene.

Specifically, the insertion can be carried out in accordance with an ordinary method using a restriction enzyme, ligase etc.

In the desired recombinant expression vector, an intron enhancer and a 3'EHS3b/4 enhancer may be constructed in the same direction from 5' end toward 3' end, in the same direction from 3' end toward 5' end, or in the opposite directions from 5' end toward 3' end and from 3' end toward 5' end.

In the above DNA construct, the interval between the promoter and the 3'EHS3b/4 enhancer intervening an exogenous DNA may be 0.1 Kb to 100 Kb, preferably 1 Kb to 10 Kb, more preferably 2 Kb to 5 Kb.

An example of preferable expression vector is retrovirus vector. More specifically, pIND (Invitrogen), pcDNA3.1/His (Invitrogen), pEGFP-N, pEGFP-C (Clontech), etc. can be illustrated.

An example of the DNA construct containing (a) promoter and (c) intron enhancer is an expression vector containing $V_H$ promoter and intron enhancer according to the present inventor and others (Azuma, T. et al., Int. Immunology, 5(2) 121-130 (1993)). It is preferably used for preparing the DNA construct.

In the above expression vector containing a promoter and an intron enhancer, the promoter is positioned 5' side upstream of the exogenous gene ordinary induced, and the exogenous gene, an intron enhancer follow in this order.

When the above vector for preparing the present DNA construct containing an exogenous gene is modified to contain a promoter, a cloning site for the insertion of desired exogenous gene, one or more enhancer necessary for inducing mutation (especially immunoglobulin enhancer as well as intron enhancer) and DNaseI sensitive region, it is effective as a DNA construct in a production process for an exogenous gene mutant or in a kit for producing an expression product of mutant gene.

The present DNA construct may be a circular DNA or a linear DNA.

The checking of whether the present DNA construct is attained can be conducted by an ordinary method, for example, by cleaving the construct with a restriction enzyme and subjecting it to the electrophoresis, or by combining PCR, Southern hybridization and sequencing, etc.

Production Process for Mutant

In a production process for an exogenous gene, first, the DNA construct resulting from the above method is introduced into a suitable host cell to obtain a homologous recombinant.

Examples of the host cell include eukaryotic organisms comprising cells of mammalian, yeast, plant and the like, but animal cells of mammalian are preferable. Preferably used as such cells are established cell lines to be transformed together with a determinant that can make the mutation more effective, COS cells from monkey (Cell, 23, 175 (1981)), Chinese hamster oocyte, Hela cells, RatII fibroblast, alimentary canal epithelium cells and its dihydrofolate reductase defectives (Proc. Natl. Acad. Sci., USA. 77: 4216 (1980)). In the case of an established cell line, it is preferable to use but not limited to, for example T cell or B cell line animal cells, especially pre-B cell line animal cells, more specifically J558 cells and J558L cells. In the case of yeast cells, yeast cells belonging to the genus Saccharomyces etc. are used. In addition, cells from animal living body can be also used as host cells.

As a result of introducing an exogenous gene into the genome of a host cell, a transformant transformed by the DNA construct of the present invention can be obtained.

Such introduction of the present DNA construct into a cell can be carried out in accordance with various methods known in the art of introducing DNA into a cell, for example, electroporation method, calcium phosphate coprecipitation method, liposome method, DEAE dextran method, microinjection method, virus transduction, etc. The electroporation method is preferably employed.

Examples of the cells to which the present DNA construct is introduced are fertilised ovum, embryo, germ cells and the like. The introduction into cells can be performed in accordance with an ordinary method.

Whether a mutant is obtained or not can be checked by known method, e.g. by random sequence method or by determining the activity of the product expressed by an exogenous gene and selecting the one whose activity is different from that of the exogenous gene. Alternatively, it can be selected based on the standard activity and its degree, or on whether the activity is high or low.

The isolated form of the cell itself containing a random mutated gene transformed with the object exogenous DNA can be improved peptides having a better function related to human exogenous gene. Therefore, it can be utilized as a pharmaceutical for improving the state of disease and as a model system for the therapeutic study.

The resulting transformant can be cultivated in accordance with an ordinary method. As a result of the cultivation, the object protein of the invention encoded by a mutant of exogenous gene is expressed and produced (accumulated, secreted) intracellularly, extracellularly or on the cell membrane of the transformant.

Various common cultures can be appropriately selected depending on the adopted host cells and used for the cultivation, and the cultivation can be carried out under the suitable condition for the growth of the host cell.

The recombinant protein of the invention thus obtained can be separated and purified if desired, by various separation procedures utilizing physical or chemical properties of the recombinant protein (Refer to e.g. Biochemistry Data Book II, 1175-1259, Edition 1, Issue 1, published by Tokyo Kagaku Dojin (Jun. 23, 1980); Biochemistry, 25(25), 8274 (1986); Eur. J. Biochem., 163, 313 (1987), etc).

Specifically illustrated as the above procedure are common reconstitution processing, processing by protein precipitant (salting out method), centrifugal separation, osmotic shock method, ultrasonication, ultrafiltration, molecular sieve chromatography (gel filtration), adsorption chromatography, ion exchange chromatography, affinity chromatography, various liquid chromatographies such as high performance liquid chromatography (HPLC), dialysis, and a combination thereof. For example, affinity chromatography using a column bonded with antibodies specific to the protein of the invention is particularly preferable.

Thus the present recombinant expression vector is expressed in an animal cell to give an exogenous DNA, resulting in random mutants encoded by said DNA. The frequency of random mutants by the recombinant expression vector of the invention is at least about $1 \times 10^{-4}$ to about $1 \times 10^{-3}$/bp/generation.

The present invention provides a production process for a mutant comprising an eukaryote, especially an animal cell containing the above recombinant vector having an insertable site of an exogenous DNA or an exogenous gene to achieve the expression of an introduced DNA sequence or a gene mutant.

According to the present production process for a mutant, a peptide having an antimicrobial activity but unavailable because of its toxicity to animal cells can be improved to provide an antimicrobial peptide having low toxicity to animal cells and higher antimicrobial activity. Similarly, it is possible to make an attempt to improve or change the functions of proteins such as naturally occurring interferon, growth hormone and the like. Therefore, a useful method for developing agrochemicals or improving the function of pharmaceuticals or the like can be provided.

Moreover, the invention provides: a kit for a production process of an exogenous gene mutant; or producing an expression product of mutant gene, comprising a DNA construct having an insertable site of an exogenous DNA or an exogenous gene. Specifically, the DNA construct comprises:

(a) a promoter;
(b) an exogenous gene-insertion site;
(c) an intron enhancer; and
(d) an enhancer comprising HS3b and/or HS4, if necessary further HS1 and HS2, in DNaseI sensitive region.

According to the present kit for producing a mutant, an improved antimicrobial peptide with low toxicity to animal cell and higher antimicrobial activity and protein pharmaceuticals with improved functions such as naturally occurring interferon, growth hormone and the like can be provided.

Antisera from Balb/c mouse and RAG-2$^{-/-}$ mouse were used as controls in A, and a culture supernatant of J558L in addition to these sera were used as controls in B.

Figure 3:
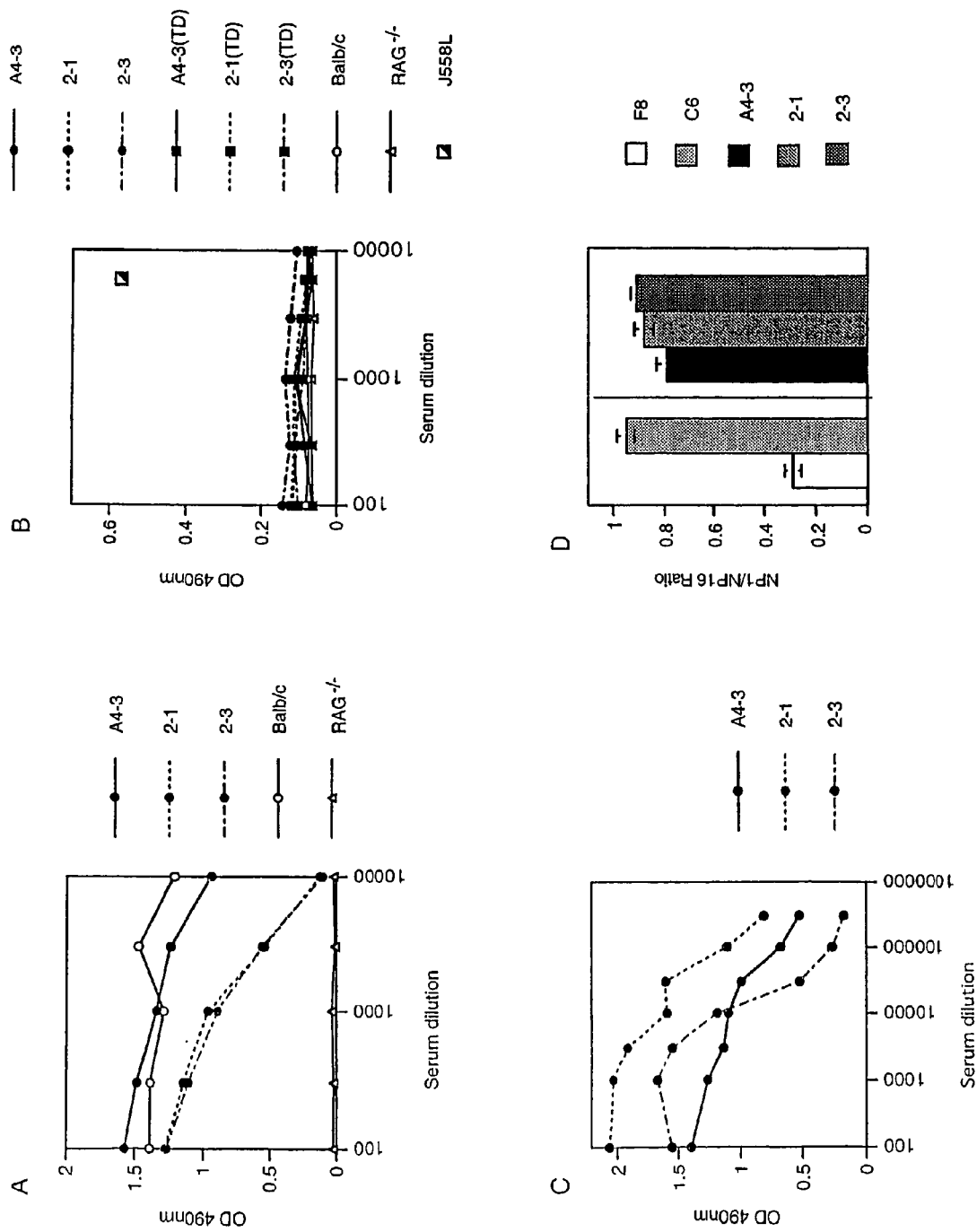
FIG. 3A shows a reconstitution of RAG-2$^{-/-}$ mouse immune systems by ES cells in chimeric mice A4-3, 2-1 and 2-3. Levels of mouse IgM in pre-immune mice were measured by ELISA using plates coated with rat anti-mouse IgM monoclonal antibody and POD-labeled goat anti-mouse IgM antibody.
FIG. 3B shows a measurement of levels of human IgM in preimmune or immune sera using plates coated with mouse anti-human IgM antibody and POD-labeled goat IgM antibody. Immune sera are referred as TD.

FIG. 3C shows an analysis of bindings of anti-NP antibodies to plates coated with anti $NP_9$-BSA antibody. Bound antibodies were detected using POD-labeled anti-mouse IgG.

FIG. 3D shows binding ratios of antisera from chimeric mice to plates coated with $NP_1$-BSA or $NP_{12}$-BSA.

Figure 4:
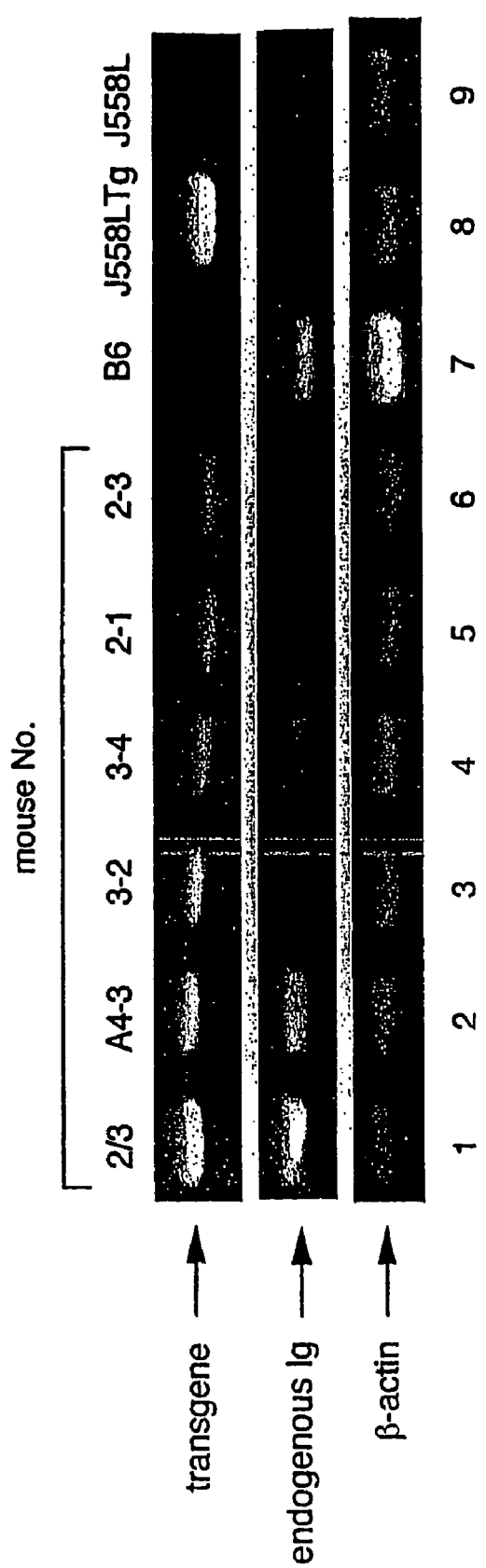

FIG. 4 shows a specific amplification of transgenes by RT-PCR. cDNA prepared from mRNA of IgM-B220$^+$ spleen cells from the chimeric mice immunized with $NP_{34}$-CGG was amplified by PCR. Only chimeric mice gave bands corresponding to the transgenes (lanes 1-6), and C57BL/6 mice did not (lane 7). J558L cell transfectant (lane 8) and non-transfectant (lane 9) are also shown as positive or negative controls.

Figure 5:
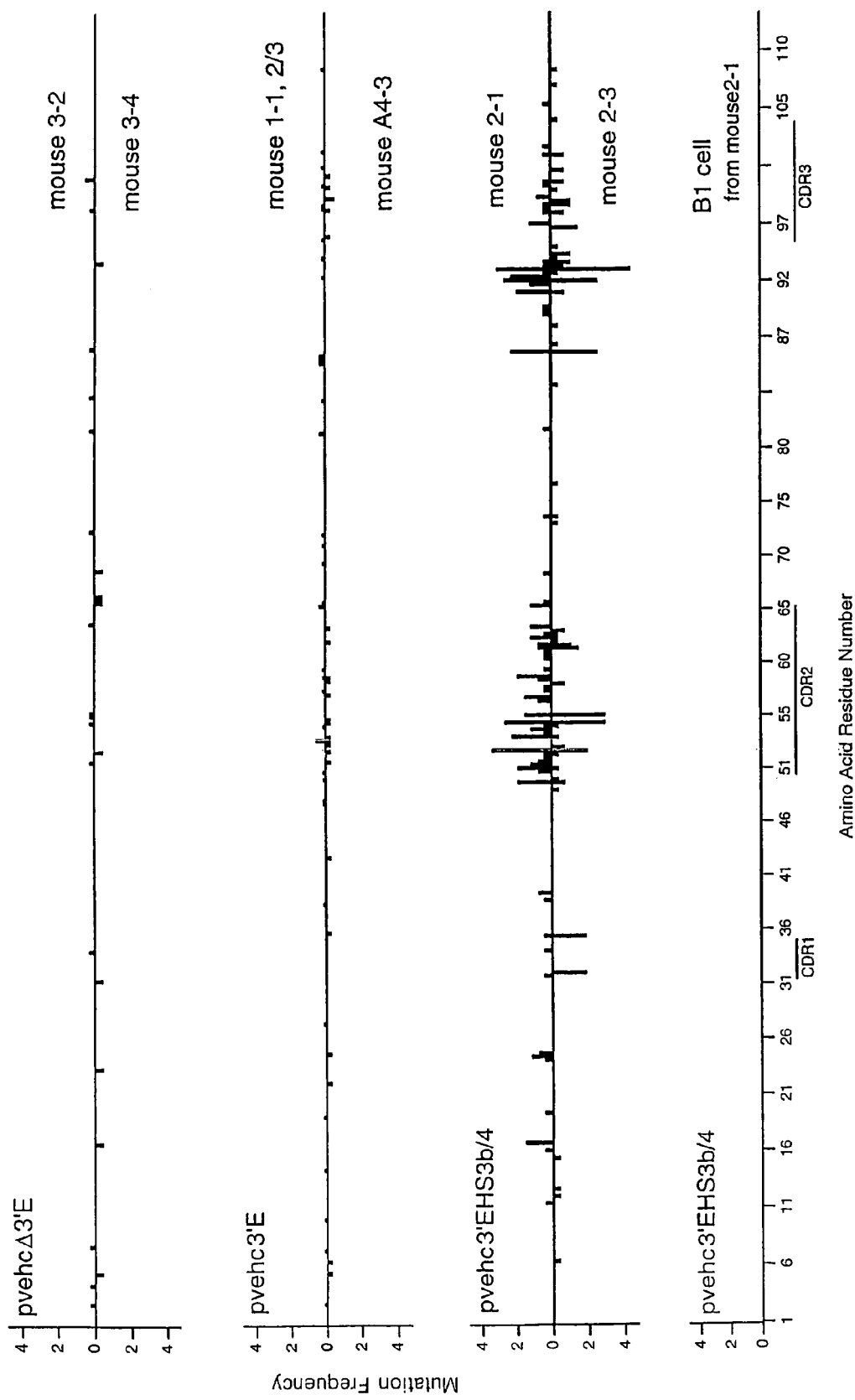

FIG. 5 shows a comparison of distribution and frequency of somatic hypermutation in transgene constructs from spleen IgM-B220+cells (A) and peritoneal B1 cells (B).

The distribution and frequency of somatic hypermutation in transgene constructs from two chimeric mice are shown separately in A. The scale at the bottom indicates the amino acid position numbered according to the method of Kabat et al.

BEST MODE FOR CARRYING OUT THE INVENTION

Examples are given below to illustrate the present invention in further detail, but they are not intended to limit the scope of the invention.

EXAMPLE 1

1) Construction of IgH Transgenes

H-chain of Ig (IgH) carrying human Cμ with different 3' flanking regions were constructed.

Acquisition of Fragment Containing $V_H$ Promoter and Fragment Containing Eμ/MAR A fragment containing $V_H$17.2.25 promoter (0.55 kb: SEQ. No. 14) with restriction enzymes KpnI and ApaI sites and another fragment containing Eμ/MAR (1 kb) with restriction enzymes XhoI and SalI sites were cloned by PCR from the construct [plasmid having chloramphenicol acetyl transferase (CAT) gene controlled by $V_H$ promoter derived from $V_H 17.2.25$ and by intron enhancer (J-C intron enhancer/matrix attachment region (abbreviated to Eμ/MAR)) between restriction enzymes XbaI and XhoI sites of pBluescript SK(+)], which the present inventor previously prepared for generating CAT transgenic mice (Azuma, T., et al., Int. Immunology, 5(2) 121-130 (1993)).

Acquisition of $V_H$-D-$J_H$ Gene Fragment

The rearranged $V_H$-D-$J_H$ gene fragment (2.0 kb) containing restriction enzymes ApaI and XhoI sites was also cloned by PCR using a genomic DNA from A6, a hybridoma producing anti-(4-hydroxy-3-nitrophenyl)acetyl monoclonal antibody (hereafter referred to as anti-NP monoclonal antibody) that is obtained from C57BL/6 mouse (Tokyo Animal Center) (Taketani, M., et al., Mol. Immunity, 32, 983 (1995): Furukawa, k., et al., Immunity, 11, 329 (1999)).

These were cloned into Bluescript II SK (from Stratagene) in order of $V_H$ promoter, $V_H$-D-$J_H$ gene and Eμ/MAR.

Acquisition of Human Cμ Gene

A 6.9 kb XbaI fragment of human Cμ gene was obtained from a phage clone, CH.H.Igμ-24 (Takahashi, N., et al., Nucleic Acids Res., 8, 5983 (1980); Health Science Research Resources Bank).

Acquisition of 3' Enhancer

A plasmid (Lieberson, R., et al., EMBO. J, 14, 6229 (1995)) containing XbaI fragment (4.0 kb) of 3' enhancer (hereafter abbreviated to 3'E) was obtained from Drs. J. Manis and F. Alt (Harvard Medical School). Fragments containing HS3b (1.2 kb) indicated as SEQ No. 1 and HS4 (1.4 kb) indicated as SEQ No. 2 were cloned by PCR using primers indicated as SEQ No. 3 to 6 and genomic DNA from a B cell lymphoma, MPC11 (Madisen, L. and Groudine, M., Genes Dev. 8, 2212 (1994)). In each primer sequence, recognition site for SpeI or XbaI restriction enzyme is underlined.

```
                                         SEQ NO. 3:
HS3-S:      5'-TCTAGAACCACATGCGATCTAAGGGATATTGGGG-3'

SEQ NO. 4:
HS3-anti    5'-CAGGACTAGTGATCATTGAGCTCCGGCTCTAAC-3'
SpeI:

SEQ NO. 5:
HS4-S XbaI: 5'-CTAGTCTAGACTGCAGACTCACTGTTCACCATG-3'

SEQ NO. 6:
HS4-anti    5'-GTGGACTAGTAAGCTTGGAGTTAGGTGGGTAGG-3'
SpeI:
```

These fragments were linked to the 3' end of 3'E, in order of HS3b and HS4. 3'E, HS3b and HS4 were linked in tandem without any intervening Ig intron sequences inserted.

Using each fragment above, three kinds of constructs pvehcΔ3'E (12 kbp), pvehc3'E (16 kbp) and pvehc3'EHS3b/4 (19 kbp) were obtained by means of gene recombination technique.

2) Structural Features of Transgenes

The transgene constructs obtained in this invention contain V region encoded by mouse $V_H 186.2$, a dominant $V_H$ involved in the response to (4-hydroxy-3-nitrophenyl)acetyl haptens (Bothwell, A. L. M., et al., Cell, 24, 625 (1981)).

The mouse $V_H 186.2$-DFL16.1-$J_H 2$ gene rearranged from A6, a hybridoma producing monoclonal antibody against (4-hydroxy-3-nitrophenyl)acetyl (Taketani, M., et al., Mol. Immunity, 32, 983 (1995): Furukawa, k., et al., Immunity, 11, 329 (1999)), was linked to human Cμ, thereby facilitating a discrimination between encoded transgene and endogenous mouse H.

In addition, as the expression of transgenes on B cell surface might change the development of the B cell, transmembrane exon was removed from Cμ to prevent the expression of transgenes on the cell surface. The transgenes contained only Cμ but not gene regions encoding other H chain isotypes.

Figure 1:
FIG. 1A shows a schematic view of IgH mutant transgene constructs used to generate chimeric mice.
In FIG. 1B, locations and directions of primers used to amplify the cDNA are shown by arrows.
Figure 1:
Figure 1:
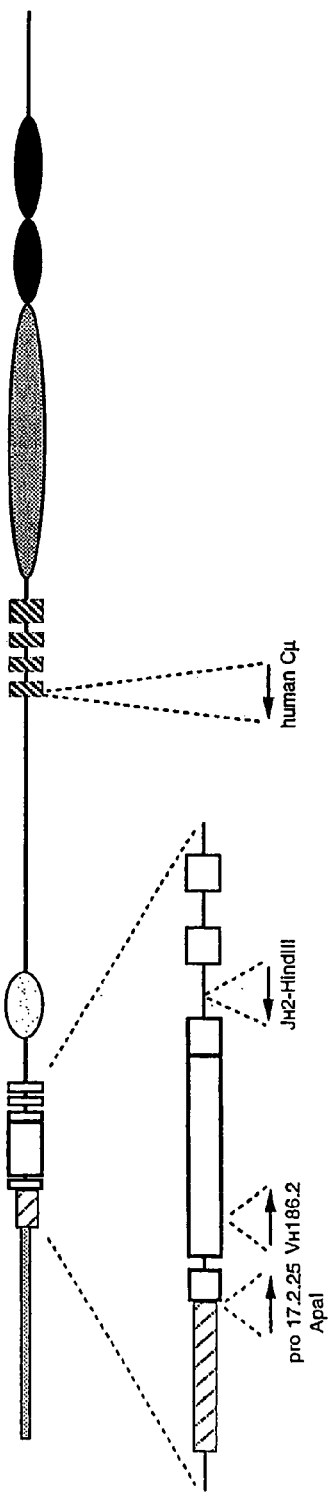
Figure 1:
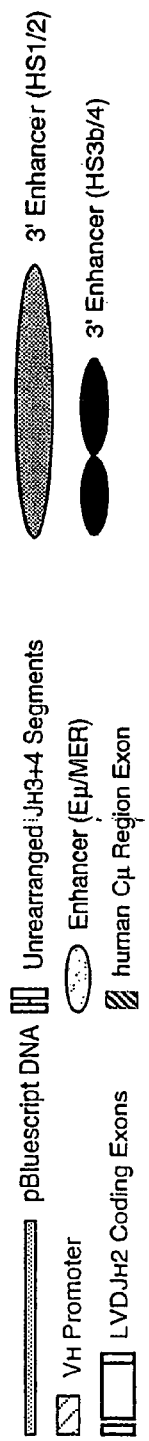

All three kinds of transgene construct contained $V_H$ promoter and Eμ/MAR from mouse J-Cμ intron as cis-acting elements, which had been used for CAT transgene construction (Azuma, T., et al., Int. Immunol., 5, 121 (1993)). Therefore, differences in the structure of the transgenes were restricted to the 3' flanking region (FIG. 1).

One of the constructs, pvehcΔ3'E, lacked 3' enhancer region and was driven by $V_H$ promoter and Eμ/MAR. Another construct, pvehc3'E, contained 3' enhancer (Lieberson, R., et al., EMBO. J., 14, 6229 (1995)) in addition to $V_H$ promoter and Eμ/MAR. The restriction enzyme BamHI fragment (4.0 kb) containing 3' enhancer (3'E) was used for the gene construction. The addition of HS3b and HS4 to pvehc3'E gave rise to a construct referred to as pvehc3'EHS3b/4.

Endogenous IgH genes contained an additional cis-acting element, referred to as HS3a (Matthias, P. and Baltimore, D., Mol. Cell Biol., 13, 1547 (1993)), -which has an identical nucleotide sequences to those of HS3b but was in an inverted form (Arulampalam, V. et al., Immunol. Today, 18, 549 (1997)). The transgene constructs of the present invention did not contain this cis-acting element.

EXAMPLE 2

1) Transfection of IgH mutant Genes (Lundblad, A. et al. Immunochemistry 9, 535-544 (1972)) into J558L Cells and Antibody Production To estimate the transcriptional activity of these three constructs, the constructs were transfected into a mouse plasmacytoma cell line, J558L cells. Linearized IgH gene constructs (10 μg) having a restriction enzyme NotI recognition site were subjected to electroporatation (Sahagaw, B. G. et al. 1986, J. Immunol., 137; 1066-1074) into J558L cells together with a plasmid pSV2-gpt (1.6 μg) (Mulligan, R. C. & Berg P. Science 209; 1422-1427 (1980)). Specific condition of the electroporation is as follows.

Instrument: Gene Pulser (BIO-RAD Laboratories)
Conditions:
  Buffer: PBS
  Cells: J558L $2 \times 10^7$ cells/ml in 0.5 ml PBS
  Linearized DNA: IgH transgene (10 μg) and pSV2-gpt (1.6 μg)
  Reaction condition: capacitance (960 μF), voltage (350V)

The transfected cells were cultivated at 37° C. in the presence of $CO_2$ (5%) and a mixture of hypoxanthine, xanthine and mycophenolic acid (Sigma). Limiting dilution of transformants of a drug resistant IgH gene was carried out, and clones were selected based on antibody production. Specifically, the production of anti-NP chimeric antibody was measured by ELISA (FIG. 2).

For the quantitative analysis of antibody production, some clones of transformant induced from each transgene construct were cultivated for 12 hrs in a flat-bottomed 96-hole plate with RPMI1640 medium (total volume: 200 μl; Nissui Pharmaceutical Co., Ltd.) containing 10% fetal bovine serum (FCS), at the concentration of $2 \times 10^6$ cells/ml. The culture supernatant diluted to various concentration with phosphate buffer saline (PBS) containing 1 mg/ml bovine serum albumin (BSA) was analyzed by ELISA using a polyvinyl plate coated with $NP_9$-BSA. Peroxidase (POD)-labeled anti-mouse $\lambda_1$ chain antibody (Southern Biotech) or anti-human μ chain antibody (ZYMED) was used for detecting bound antibodies.

Figure 2:
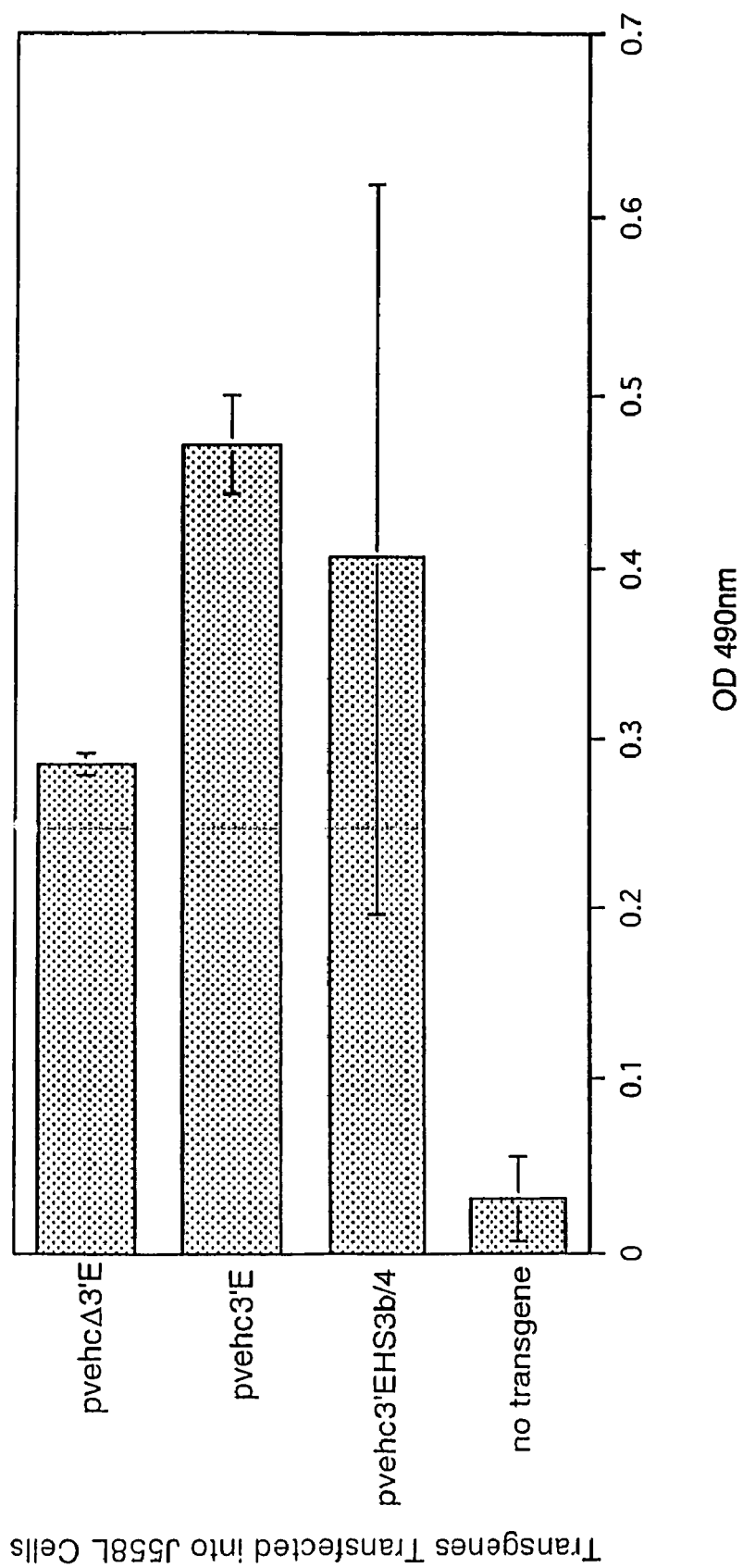
FIG. 2 indicates the production of anti-NP antibodies producing human Cμ from J558L cells transfected with the IgH mutant genes shown in FIG. 1. The supernatants of transfected J558L cells ($1 \times 10^6$ cells/ml) cultivated for 12 hrs were subjected to ELISA using plates coated with $NP_9$-BSA for estimating the antibody production.

The result is shown in FIG. 2.

Transgene constructs were designed to encode chimeric H-chains, possessing the $V_H$ region from a mouse anti-NP monoclonal antibody and the C region from human Ig, which were expected to assemble with mouse $\lambda_1$ chains and give rise to anti-NP chimeric antibody.

All constructs were actively transfected in J558L cells and produced anti-NP antibodies by pairing with endogenous $\lambda_1$-chains. Among these constructs, pvehcΔ3'E showed rather weaker production compared with the others. The addition of 3'E (pvehc3'E) resulted in a significant increase in antibody production, however, further addition of HS3b and HS4 seemed to have no effect on antibody production. Although little information was available concerning the dependence of transcription on the copy number of each transfected DNA, the inventor assumed that the amount of antibody production reflected the transcriptional activity of the constructs, which did not differ significantly between pvehc3'E and pvehc3'EHS3b/4.

EXAMPLE 3

1) Generation of Chimeric Mice

To generate chimeric mice, the present inventor employed at least two independent transfected ES clones for the microinjection into $RAG-2^{-/-}$ mouse blastocysts. The inventor also used at least two chimeric mice/transgene constructs for the analysis of somatic hypermutation. The transfected ES cell lines and the chimeric mice used in this experiment are shown in Table 1.

The EcoRI fragment of pGKneo (1.5 kb, 1 μg) and the three kinds of linear-chain IgH transgene constructs (30 μg) in the same manner as in Example 2 were electroporated into $1\times10^7$ of E14-1 cells (Kuhn, R. et al., Science, 254, 707 (1991)) using a Bio-Rad Gene Pulser.

The transfected cells were then selected with G418 (150 μg/ml, Gibco). The selected colonies were screened by: PCR using two primers indicated as SEQ. No. 7 and 8 that can be hybridized to DNA sequences located in the $V_H17.2.25$ promoter and $J_H2$; and Southern blotting using human Cμ gene as a probe, respectively.

SEQ. No. 7:
5'-GACTCAGGAGGACTCTAGTT-3'

SEQ. No. 8:
5'-GGTGTCCCTAGTCCTTCATG-3'

PCR amplification was performed for 30 cycles of 95° C. for 30 sec, 65° C. for 30 sec and 72° C. for 1 min. The copy number of integrated pvehc3'E was calculated to be 2 to 3 by Southern blotting. The copy numbers of other transgenes pvehcΔ3'E and pvehc3'EHS3b/4 were estimated by the PCR analysis using DNA from pvehc3'E-transfected ES cells as a standard.

2) Antibody Production by Chimeric Mice

ES cell clones containing the IgH transgene were injected into blastocysts from $RAG-2^{-/-}$ mice (Takahashi, N. et al., Nucleic Acids Res., 8, 5983 (1980)) and transplanted into uteri of ICR foster mothers (8 to 12 week old, CLEA Japan Inc.). Complementarity of the immune system by B cells and T cells originated from ES cells in chimeric mice was tested by flow cytometry after staining the cells with PE anti-CD3 antibody or biotin anti-B220/SA-FITC.

POD-labeled sheep anti-mouse u-chain antibody was used for the detection of bound antibodies. For analyzing antibodies having human Cμ, plates were coated with sheep anti-human IgM antibody (Southern Biotech) and POD-labeled anti-human IgM monoclonal antibody (ZYMED) was used for detecting bound antibodies. The culture supernatant of J558L transformant, human Waldenstrom IgM, and anti-NP IgM monoclonal antibody B4-3 were used as control antibodies.

TABLE 1

| | Used ES cells and chimeric mice | | |
|---|---|---|---|
| Construct | Cell clone | Copy number | Chimeric mouse |
| pvehcΔ3'E | 3-89 | <3 | 3-2 |
| | 3-88 | <3 | 3-4 |
| pvehc3'E | No. 6 | <3 | 1-1,2/3 |
| | A-4 | <3 | A4-3 |
| pvehc3'EHS3b/4 | 25-2-5 | <3 | 2-1 |
| | 25-2-2 | <3 | 2-3 |

A backcross with C57BL/6 mouse was carried out to examine the germinal transmission of the transgene, and the DNA was extracted from the tail of the resulting mouse to analyze the generation of chimeric mouse based on whether the transgene was contained or not.

3) Immune and Antibody Production

In order to examine whether the immune system was reconstituted with the lymphocytes derived from ES cells, the amounts of IgM in the pre-immune sera of chimeric mice A4-3, 2-1, and 2-3 were measured by ELISA.

The result is shown in FIG. 3A. Irrespective of the kind of transgene, detected amounts of mouse IgM in all the sera from these mice were similar, but smaller than that in a normal BALB/c mouse.

Next, $NP_{34}$-chicken γ globulin ($NP_{34}$-CGG) and NP-BSA having a different NP value were prepared in the same manner as in Azuma et al. (Azuma, T. et al., Molec. Immunol., 24, 287 (1987)).

CFA (complete Freund's adjuvant: Difco, 100 μg/mouse) including (4-hydroxy-3-nitrophenyl)acetyl chicken γ globulin (hereafter referred to as $NP_{34}$-CGG) was administered to the chimeric mice, and the same amount of additional immune was administered using IFA (incomplete Freund's adjuvant). Three days after final administration of PBS including $NP_{34}$-CGG, antisera were collected from the immunized mice. The mice were then sacrificed and tissue samples were obtained.

Plates coated with $NP_1$-BSA or $NP_{16}$-BSA were used for measuring the production of anti-NP antibodies and the affinity maturation of these antibodies. POD-labeled sheep anti-mouse IgG (ZYMED) was used for detecting the antibodies.

Anti-NP monoclonal antibody, F8, was used as a control for an immature antibody, and C6 as a control for a matured monoclonal antibody (Taketani, M. et al., Mol. Immunol., 32, 983 (1995); Furukawa, K., et al., Immunty, 11, 329 (1999)).

The result is shown in FIG. 3B. The antibody expressing human Cμ encoded by the transgenes in the pre-immune or immune antisera from the mice immunized with $NP_{34}$-CGG was not detected.

Hybridomas producing anti-NP monoclonal antibody (γ1λ1) were prepared from pvehc3'EHS3b/4 mice immunized with $NP_{34}$-CGG. None of these secreted antibodies expressed human Cμ, however, some of them synthesized intracellular H-chain having human Cμ.

The result suggests that the transgenes were transcribed and translated in the B cells of chimeric mice. However, the secreted H-chain products level was lower than the detectable level.

Next, antibody reaction of chimeric mice against TD antigen $NP_{34}$-CGG was examined by ELISA. The result is shown in FIG. 3C. The antibody value changed, but all the mice produced anti-IgG antibodies indicating that the immune systems respond to the anti-NP antibody production.

Furthermore, the binding ratio of these antibodies to $NP_1$-BSA, which relates to the binding to $NP_{16}$-BSA, was examined as the measurement of affinity maturation. The result is shown in FIG. 3D.

As shown in FIG. 3D, a control monoclonal antibody F8 showed no somatic hypermutation and had an association constant (Ka) of $2\times10^5$/M with NP-Cap, and the ratio was 0.29. On the other hand, well matured monoclonal antibody C6 having $2\times10^7$/M of Ka (Furukawa, K. et al., Immunity, 11, 329 (1999)) had the ratio of around 1. All the sera from chimeric mice showed similar ratios to that of C6, therefore the affinity maturation of anti-NP antibodies advanced to the similar extent in all chimeric mice after immunized with $NP_{34}$-CGG.

EXAMPLE 4

Cloning and Sequencing of $V_H$ Gene

Although the immune system was reconstituted in the chimeric mouse, it was rather difficult to obtain sufficient amount of $PNA^{hi}IgG^+B$ cells, which are popular as germinal center cells derived from a single chimeric mouse. Accordingly, after immunization with $NP_{34}$-CGG, spleen $IgM^- B220^+$ cells, which are expected to select isotype-switching memory B cells, XX were sorted by flow cytometry using a FACS Vantage.

The single-cell suspension from spleen of chimeric mice immunized with $NP_{34}$-CGG were treated with 0.83% of ammonium chloride to induce hemolysis. In some experiments, T cells were also treated with anti-Thy1 antibody (T24/40 and HO13.4) to induce hemolysis, and then treated with a rabbit complement. The cells were stained with phycoerythrin (PE)-labeled anti-CD45R/B220 (cell surface molecule, pherMingen) or fluorescein isothiocyanate (FITC)-labeled anti-mouse IgM (ZYMED).

The peritoneal cells were stained with biotin-labeled anti-CD5/FITC-labeled streptavidin (pherMingen) and PE-labeled anti-CD45R(B220).

The $CD45R(B220)^+IgM^-$, $CD45R(B220)^+IgM^+$, or $CD5^+ CD45R(B220)^+$ cells were fractioned by flow cytometry on a fluorescence activated cell sorter (FACS) Vantage (Becton, Dickinson and Company).

In addition, as a control experiment, CD4+ cells and/or CD8+ cells were obtained from the thymus after staining and sorting.

Total RNA was prepared from spleen or peritoneal cells fractioned by the above cytometry, using TRIzol (RNA preparation reagent, GIBCO BRL) according to the manufacturer's instructions.

The cDNA was prepared from the total RNA using oligo (dT) as a primer and Superscript II reverse transcriptase (GIBCO BRL). The cDNA samples were each PCR-amplified using: $V_H$186.2 primer of SEQ. No. 9 and human Cμ primer of SEQ. No. 10 for the transgenes; and $V_H$186.2 primer of SEQ. No. 9 and mouse Cγ1 primer of SEQ. No. 11 for endogenous mouse Ig genes, respectively.

SEQ. No. 9:
5'-CATGCTCTTCTTGGCAGCAAC-3'

SEQ. No. 10:
5'-GCAGCCAACGGCCACGCTGC-3'

SEQ. No. 11:
5'-GGCCGAATTCCATGGAGTTAGTTTGGG-3'

The PCR reaction was carried out under the condition of 95° C. for 1 min, 62° C. for 1 min and 72° C. for 1 min for 30 cycles. PCR products of the transgenes and endogenous mouse IgH genes were analyzed by agarose gel electrophoresis or ligated into pCR-2.1 (Invitrogen Corporation) using TA cloning kit (Invitrogen Corporation) and sequenced using M13 primer shown as SEQ. No. 12 (−20, Takara Bio Inc.), M13 reverse primer shown as SEQ. No. 13 (Takara Bio Inc.) and Hitachi DNA sequencer model 5500 (Hitachi, Ltd.).

As shown in FIG. 4, the expression of antibody fragments including transgenes was identified.

2) Somatic Hypermutation of Transgenes in Spleen or Peritoneal B Cells

The frequency of mutation was calculated by dividing the total of mutation by the total of sequence-determined base. The result is shown in Table 2.

TABLE 2

Mutations in V region sequences of spleen $IgM^-$ B cells of chimeric mice

| | Construct | | | | | |
|---|---|---|---|---|---|---|
| | pvehcΔ3'E | | pvehc3'E ES clone | | pvehc3'EHS3b/4 | |
| | 3-89 | 3-88 | No.6 | A4 | 25-2-5 | 25-2-2 |
| Number of sequence analyzed | 30 | 18 | 51[c] | 30 | 21 | 21 |
| Number of mutation observed | 16 | 11 | 42 | 25 | 161 | 132 |
| Percent of mutation in CDR[a] (%) | 56 | 36 | 38 | 75 | 57 | 55 |
| Mutation frequency[b] (%) | 0.15 | 0.17 | 0.23 | 0.23 | 2.14 | 1.76 |

[a]Percent of mutation in CDR = 100 × (total number of point mutations in CDR)/(total number of point mutations)
[b]Mutation frequency = 100 × (total number of point mutations)/(total number of base pairs)
[c]Two chimeric mice were analyzed.

For the somatic hypermutation in transgenes, primers to hybridize with either $V_H$186.2 or human Cμ were used. Cloning and sequencing of the cDNA prepared by RT-PCR were conducted. The result is shown in Table 3. The distribution and frequency of somatic hypermutation among the transgene constructs in spleen B cells are shown in FIG. 5.

Specific amplification of the transgenes due to the combined use of the primers was observed only in the spleen cells from chimeric mice, but not in those from C57BL/6 mice immunized with $NP_{34}$-CGG. In addition, it was observed that all the sequences have an identical junctional diversity in CDR3 that is a characteristic of A6DNA used to construct transgenes.

As to the gene construct pvehγ3'E, nucleotide changes resulting from somatic hypermutation were observed in $V_H$186.2-DFL16.1-$J_H$2, but the frequency was low. The frequency of mutation was estimated to be 0.17% (Table 2).

The gene construct pvehc3'E showed an essentially similar distribution of hypermutation, although the frequency increased slightly compared to that of pvehcγ3'E (Table 2).

In the case of pvehc3'EHS3b/4, where HS3b/4 is further added to the gene construct pvehc3'E of the invention, a dramatic increase of the frequency of somatic hypermutation was shown as a result in $V_H186.2$-DFL16.1-$J_H2$ gene (FIG. 5). All the sequenced PCR clones contained nucleotide changes in spite of the fact that they were selected randomly. These nucleotide changes were found with high frequency in the area around CDR2 (hypervariable region 2) and CDR3 (FIG. 5 and Table 2).

The data were obtained from two chimeric mice corresponding to each transgene construct shown in FIG. 5, and were in good agreement with each other. A high frequency of hypermutation was apparent in pvehc3'EHS3b/4. However, mutation was clearly absent in peritoneal B1 cells from the same chimeric mouse (FIG. 5).

The following Table 3 shows characteristics of substitutions identified in the transgenes.

TABLE 3

Mutations in IgH gene

| Substitution | Construct | | |
|---|---|---|---|
| | pvehcΔ3'E | pvehc3'E | pvehc3'EHS3b/4 |
| Transition | | | |
| A→G | 5 | 12 | 25 |
| G→A | 3 | 13 | 47 |
| C→T | 1 | 5 | 8 |
| T→C | 3 | 5 | 34 |
| Total | 12 | 35 | 114 |
| Transversion | | | |
| C→A | 2 | 0 | 8 |
| G→T | 1 | 2 | 20 |
| A→C | 2 | 2 | 32 |
| A→T | 0 | 5 | 12 |
| G→C | 4 | 7 | 43 |
| C→G | 1 | 4 | 11 |
| T→A | 4 | 7 | 26 |
| T→G | 1 | 3 | 27 |
| Total | 15 | 32 | 179 |

It was clear from the comparison between IgH transgenes that the base transition and base transversion arise with almost the same frequency.

In addition, in the locus sequence named as RGYW motif (A/G, G, C/T, A/T) (Kabat, E. A. et al., US National Institutes of Health, Bethesda, Md., U.S.A., p1394, (1991): Rogozin, I. B. et al., Biochim. Biophys. Acta., 1171, 11 (1992)), the emergence of somatic hypermutation in $V_H186.2$ transgene was analyzed. The germline gene $V_H186.2$ (294 bp) contained RGYW/WRCY motif (93 bp) corresponding to 32% of the total bases, and the frequency of somatic hypermutation in this motif appeared to be 34%, which is not significantly higher than those in the other $V_H$ regions.

INDUSTRIAL APPLICABILITY

In the above Examples, the present inventor employed a RAG-2$^{-/-}$ blastocyst system to prepare chimeric mice carrying IgH transgenes with different cis-acting elements.

The producing method of the invention has some advantages over conventional transgene techniques and is superior especially when ES cells are transformed with law copy numbers of transgene. In fact, the copy number of transgene in transformant ES cells was calculated to be 3 or less in most cases by Southern blotting and PCR (Table 1).

Only a marginal numbers of hypermutation was found in pvehcΔ3'E and the finding was confirmed that the cis-acting elements, $V_H$ promoter and Eμ/MAR were not sufficient for inducing a high frequency of hypermutation. Addition of a 3' enhancer fragment (4 kb) to pvehcΔ3'E (pvehc3'E) resulted in an approximately 30% increase in the frequency of hypermutation.

In the present invention, it was found that the expression frequency of induced hypermutation was greatly enhanced by introducing HS3b and HS4 to the 3' end of 3' enhancer of pvehc3'E, which indicates that the construct pvehc3'EHS3b/4 contains all necessary elements for somatic hypermutation. The Experiments by the inventor clarified that the motifs responsible for high frequency hypermutation are within an HS3b/4 region of 2.6 kb.

Thus it is possible to provide a recombinant expression vector for inducing a random mutant of desired transgene. Moreover, it is possible to provide a production process for a high frequent random mutant obtained by expressing the recombinant expression vector in animal cells. Furthermore, it is possible to provide a method for expressing a random mutant or a kit for producing a random mutant comprising the recombinant expression vector and animal cells.

The invention claimed is:

1. A process for producing random mutants of DNA encoding an exogenous polypeptide comprising:
    (A) introducing into an animal cell a DNA construct comprising the following (i)-(iv):
    (i) a promoter;
    (ii) DNA encoding an exogenous polypeptide provided that said DNA encoding an exogenous polypeptide does not encode an immunoglobulin;
    (iii) an intron enhancer; and
    (iv) an enhancer comprising at least one of HS3b and HS4, in a DNaseI sensitive region; and
    (B) culturing the resulting animal cell whereby during said culturing said enhancer comprising at least one of HS3b and HS4 acts to produce random mutants of DNA encoding the exogenous polypeptide in the animal cell.

2. The process according to claim 1, wherein the (iv) enhancer further comprises HS1 and HS2.

3. The process according to claim 1, wherein the (iv) enhancer comprises the nucleotide sequence of SEQ ID NO: 1 and SEQ ID NO: 2.

4. The process according to claim 2, wherein the (iv) enhancer comprises HS1, HS2, HS3b and HS4.

5. The process according to claim 1, wherein the (i) promoter is a $V_H$ promoter; and
    the (iv) enhancer comprises the nucleotide sequences of SEQ ID NOs: 1 and 2.

6. The process according to claim 4, wherein the DNA construct is pvehc3'EHS3b/4.

7. The process according to claim 1, wherein the animal cell is a B cell line animal cell.

8. A method for obtaining mutants of an exogenous polypeptide comprising:
    producing random mutants of DNA encoding an exogenous polypeptide by a method comprising:
    (1) introducing into an animal cell a DNA construct comprising the following (a)-(d):
    (a) a promoter;
    (b) DNA encoding an exogenous polypeptide provided that said DNA encoding an exogenous polypeptide does not encode an immunoglobulin;
    (c) an intron enhancer; and
    (d) an enhancer comprising at least one of HS3b and HS4, in a DNaseI sensitive region;
    (2) culturing the resulting animal cell whereby during said culturing said enhancer comprising at least one of HS3b and HS4 acts to produce random mutants of DNA encoding the exogenous polypeptide in the animal cell; and
    (3) expressing said random mutants of DNA encoding the exogenous polypeptide in the animal cell so as to obtain said mutants of said exogenous polypeptide.

9. A DNA construct for producing mutants of an exogenous polypeptide, comprising the following (i)-(iv):
    (i) a promoter;
    (ii) DNA encoding an exogenous polypeptide provided that said DNA encoding an exogenous polypeptide does not encode an immunoglobulin;
    (iii) an intron enhancer; and
    (iv) an enhancer comprising at least one of HS3b and HS4, in a DNaseI sensitive region.

10. The DNA construct according to claim 9, wherein the (iv) enhancer further comprises HS1 and HS2.

11. The DNA construct according to claim 9, wherein the (iv) enhancer comprises the nucleotide sequence of SEQ ID NO: 1 and 2.

12. The DNA construct according to claim 9, wherein the (iv) enhancer comprises HS1, HS2, HS3b and HS4.

13. The DNA construct according to claim 9, wherein
    the (i) promoter is a $V_H$ promoter; and
    the (iv) enhancer comprises the nucleotide sequence of SEQ ID NOs: 1 and 2.

14. The DNA construct according to claim 9, wherein the DNA construct is pvehc3'EHS3b/4.

15. A kit for producing random mutants of DNA encoding an exogenous polypeptide or for producing an expression product thereof, comprising a vector comprising:
    (i) a promoter;
    (ii) an insertion site for insertion of DNA encoding an exogenous polypeptide;
    (iii) an intron enhancer; and
    (iv) an enhancer comprising at least one of HS3b and HS4, in a DNaseI sensitive region.

16. The kit according to claim 15, wherein the (iv) enhancer further comprises HS1 and HS2.

* * * * *

UNITED STATES PATENT AND TRADEMARK OFFICE
CERTIFICATE OF CORRECTION

| | | |
|---|---|---|
| PATENT NO. | : 7,655,466 B2 | Page 1 of 1 |
| APPLICATION NO. | : 10/481742 | |
| DATED | : February 2, 2010 | |
| INVENTOR(S) | : Takachika Azuma | |

It is certified that error appears in the above-identified patent and that said Letters Patent is hereby corrected as shown below:

Title, Item [54] should read:

-- (54) PRODUCTION PROCESS FOR ~~MUNANT~~ MUTANT --.

Item [*] Notice:

Delete the phrase "by 1131 days" and insert -- by 1694 days --.

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,466 B2 | Page 1 of 1 |
| APPLICATION NO. | : 10/481742 | |
| DATED | : February 2, 2010 | |
| INVENTOR(S) | : Takachika Azuma | |

It is certified that error appears in the above-identified patent and that said Letters Patent is hereby corrected as shown below:

Title Page, Item [54] and at Column 1, line 1, Title should read:

-- (54) PRODUCTION PROCESS FOR ~~MUNANT~~ MUTANT --.

On the Title Page:

The first or sole Notice should read --

Subject to any disclaimer, the term of this patent is extended or adjusted under 35 U.S.C. 154(b) by 1694 days.

This certificate supersedes the Certificate of Correction issued August 31, 2010.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 1182
<212> TYPE: DNA
<213> ORGANISM: Homo sapiens

<400> SEQUENCE: 1
tctagaacca catgcgatct aagggatatt ggggcaatac atgtgtagtg agatacctgc      60
ctttctgatg agccctgtct ggcagggata aactctcctt tctgcatctc cagggcctcg     120
atgagctgac tatctagtcc tctgccagaa tagctgtgtg gccttgggtg atgctggctg     180
acctcaggct ggtctgggtt gtctctggct gacacccctt gactctggat gaccctggga    240
```

| | |
|---|---|
| agaccatact taatcttaat tggacttgtt ctcattggga gagaacatgg cctcactaag | 300 |
| gcacgagtgt ggatggcctt gggtgatggg ggttggggcc tcctcagccc ctggcaggct | 360 |
| tccctggctg ccacccctca tccaggtccc aggcccacct ggcctggtcc agtgtggtgt | 420 |
| gattctcaga acagtagctg tggtttgggg cacctgtgct gagaaaggct caggatgact | 480 |
| cagctgccct cagctcagag ctgctttgaa tgtttcagca ggtgatagac aacagagact | 540 |
| tcagaagaga gaaaaacaag ttgctaatgt gaacatccct gccctacccc cacacctgta | 600 |
| ctgcaaatct ccccacactg ttgacccag atagagatcc caggacagca ggtgatagac | 660 |
| aaaggaggct ccagaggaga gaaaaatagt atctacaagc atgactacct ctgccctgcc | 720 |
| ccacacctgc cctgcaaagc tccccaggat gctgacccca tctgtaga ccccaggcca | 780 |
| gaggctccat ctcccagggc ctgggcttgc tttgtctcca ttctgcgcct ctgagcctgg | 840 |
| gcaaggccaa tgagcgaaag gggtcactgt cccagttgca gcccagtgtg tgacagtgtt | 900 |
| gtggggattc tggaatcttc tgcaggaatc ccctgtaggg atcctcctaa tgtgaatgag | 960 |
| gcttggaata gcaaagggac gtcttgtaaa ataccactga ttccttgggc ctcagacaat | 1020 |
| ggatgtgaga tgaggaccaa ggtccagggc cagtgttggt aagcagaatt tggggctaga | 1080 |
| gttcaggctt agaagtcaat gatgagggcc agggccaat gactaggtca gggcccattg | 1140 |
| atcagtacag gacccagttg ttagagccgg agctcaatga tc | 1182 |

<210> SEQ ID NO 2
<211> LENGTH: 1381
<212> TYPE: DNA
<213> ORGANISM: Homo sapiens

<400> SEQUENCE: 2

| | |
|---|---|
| ctgcagactc actgttcacc atgaacccag ctagtcagat tcatatgtga aactcatatc | 60 |
| agcctctgca cacacataca cacacataca cacatattac acccatgcac acacatgtac | 120 |
| acatacatac acatgtacac atacatgtgt acacacacat atagagaagg cattggtggg | 180 |
| gaaaacatta ggccatggct acagtacagg gcacaaggat ggtggtacag aatgaggtca | 240 |
| ggctgggtca gcataacaag aacacttgga caaagtgagg gtagtgtgtg tgtgtgtgtg | 300 |
| tgtgtgtgtg tgtgtgtgtg cacgttgaaa gtcttcagta gactggtatc actagccctg | 360 |
| atatgggcaa cacagcaagc ctgggtcaca ctcaagctga gtatcagggt agccagggcc | 420 |
| ttctaaccaa gggtagatgc agcctgtgtt ccgtttactg accagtgaga agccatgagc | 480 |
| tgaaccagac cagaagaccc ttactgttcc cacccccaccc ccacccagtt tagtctcagc | 540 |
| aagaccctgt actgtgggcc acagctctcc tctacactcc acctgtagca caaacactat | 600 |
| ttgcaaacat ttctaaaaag tagtagaaca ggaaccacag agcagagggg gggactggcg | 660 |
| tggaaagccc cattcaccca tgggactgaa actcagggaa ccagaaccgt aaggagattt | 720 |
| gcatggtgct gggggaggtt ggccctggat cagtgagccc agagagttac tggtttctca | 780 |
| cttccatcat gtcaacctcc tcaaccccca aaaatggcca ggcctaggct atggatgagt | 840 |
| ttcaatgacc aggccctaag gacgagtcac agaggacttc ctggtgggct caggcagcag | 900 |
| acctgctcag atggattgca gagccagagg gagccatggc caggaaggcc agacgcctta | 960 |
| ggggtgtgct gtctctgcat cctttgccct ctctgctcct cacagtccat ctgccatctc | 1020 |
| acaatccctg ctgtcgctct ggggcccaga cctggccagt ctgggtacct gtggaataca | 1080 |
| cccaaagaag caatccccag cctcaggatc cacaactact tccctacag acatgagtga | 1140 |

-continued

```
tctcagccca catgtctggg ggccacagaa gcccctaaga ccctactctg ctaataggcc    1200
ctcctcccac cacgcaagac aatacacagg caaggtgatg tggatgagag gaccaaccca    1260
ggtacctgtg tgtgagatac accctgtggg tatcctggcc agaatctggt gaccaaccca    1320
acctgtgtcc ctagaggagt actccgtgcc tgcactcacc tacccaccta actccaagct    1380
t                                                                    1381
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 3

```
tctagaacca catgcgatct aagggatatt gggg                                  34
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 4

```
caggactagt gatcattgag ctccggctct aac                                   33
```

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 5

```
ctagtctaga ctgcagactc actgttcacc atg                                   33
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 6

```
gtggactagt aagcttggag ttaggtgggt agg                                   33
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7

```
gactcaggag gactctagtt                                                  20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 8

-continued ggtgtcccta gtccttcatg                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
catgctcttc ttggcagcaa c                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 10
gcagccaacg gccacgctgc                                              20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 11
ggccgaattc catggagtta gtttggg                                      27

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:M13 forward
      primer

<400> SEQUENCE: 12
ctctacagac acgggcc                                                 17

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:M13 reverse
      primer

<400> SEQUENCE: 13
aaaaagcttg gtgtccctag tccttcatg                                    29

<210> SEQ ID NO 14
<211> LENGTH: 546
<212> TYPE: DNA
<213> ORGANISM: Artificial Sequence
<220> FEATURE:
<223> OTHER INFORMATION: Description of Artificial Sequence:promoter

<400> SEQUENCE: 14
ttcttaaata aaatgctgaa tgaacatttg aatacacata ttgctgagac atgttctctt    60
gctgtcattt gtgtaatatt ttagtatgca accttttgga aaggccatta ttatttaaat   120

```
atatatgaga gaagattgct aactctcata aatgtattgg ttttttttt aaatttccag    180 taagcgttat cctcattgct actaccacca atcaattttt tcactaagac aagtgagtgt    240
ctcaggttag gattctattt taagattgag atattaggct ttgatactac atctaaatgg    300
tctgtacatg tctcgaagaa agttcttcag acagagttag gacttggatc caggagttag    360
gacttggact gactcaggag gactctagtt tcttcttctc cagctggaat gtccttatgt    420
aagaaaagcc ttgcctcatg agtatgcaaa tcatgtgcga ctgtgatgat taatataggg    480
atatccacac caaacatcat atgagcccta tcttctctac agacactgaa tctcaaggtc    540
cttaca                                                                546
```